US012611220B2

(12) United States Patent
Tsinteris et al.

(10) Patent No.: US 12,611,220 B2
(45) Date of Patent: Apr. 28, 2026

(54) RECIPROCATING SERRATED BLADE FOR PRECISION DISSECTION

(71) Applicant: HOLOGIC, INC., Marlborough, MA (US)

(72) Inventors: Ion Tsinteris, Marlborough, MA (US); Taylor Zahn, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 1071 days.

(21) Appl. No.: 17/703,200

(22) Filed: Mar. 24, 2022

(65) Prior Publication Data

US 2022/0211403 A1     Jul. 7, 2022

Related U.S. Application Data

(63) Continuation of application No. PCT/US2020/055928, filed on Oct. 16, 2020.

(60) Provisional application No. 62/931,665, filed on Nov. 6, 2019.

(51) Int. Cl.
*A61B 17/32* (2006.01)

(52) U.S. Cl.
CPC .................. *A61B 17/32002* (2013.01); *A61B 2017/320028* (2013.01)

(58) Field of Classification Search
CPC .. A61B 17/32002; A61B 2017/320028; A61B 17/144; A61B 17/42; A61B 90/361; A61B 2090/306
See application file for complete search history.

(56) References Cited

U.S. PATENT DOCUMENTS 1,726,863 A     9/1929  Samuel
2,435,863 A  *  2/1948  Wydro ..................... A61C 3/02
                                                    606/177

3,189,998 A     6/1965  Beisheim et al.
5,275,607 A  *  1/1994  Lo ........................ A61F 9/00745
                                                    606/174
5,752,973 A     5/1998  Kieturakis et al.
5,766,166 A     6/1998  Hooven
(Continued)

FOREIGN PATENT DOCUMENTS

EP          3479786          5/2019

OTHER PUBLICATIONS

PCT International Search Report and Written Opinion for International Appln. No. PCT/US2020/055928, dated Jan. 21, 2021 (14 pages).

(Continued)

*Primary Examiner* — Ashley L Fishback
*Assistant Examiner* — Chima U Igboko
(74) *Attorney, Agent, or Firm* — Vista IP Law Group, LLP

(57)          ABSTRACT

A medical device includes a shaft having a distal end, a proximal end, and a shaft body extending between the distal end and the proximal end, the shaft body having a longitudinal axis; a first blade fixedly coupled to the distal end of the shaft, wherein the first blade has a first rectilinear planar surface; a second blade in contact with the first blade, wherein the second blade has a second rectilinear planar surface, and wherein the second blade is configured to move in a reciprocating manner in opposite directions that are parallel to the longitudinal axis of the shaft body; and a handle coupled to the proximal end of the shaft; wherein the shaft, the first blade, and the second blade are sized for insertion into a patient.

20 Claims, 7 Drawing Sheets

(56) References Cited

U.S. PATENT DOCUMENTS

| | | | |
|---|---|---|---|
| 6,520,960 | B2 | 2/2003 | Blocher et al. |
| 6,860,886 | B1 * | 3/2005 | Lee ..................... A61B 17/144 |
| | | | 606/82 |
| 7,563,259 | B2 | 7/2009 | Takahashi et al. |
| 8,241,322 | B2 | 8/2012 | Whitman et al. |
| 8,870,902 | B2 | 10/2014 | Deodhar et al. |
| 9,457,168 | B2 | 10/2016 | Moll et al. |
| 9,636,130 | B2 | 5/2017 | Cesarini et al. |
| 9,649,125 | B2 | 5/2017 | Truckai |
| 10,383,651 | B2 | 8/2019 | Pell et al. |
| 2013/0211321 | A1 | 8/2013 | Dubois et al. |
| 2016/0143658 | A1 * | 5/2016 | Stokes ........... A61B 17/320092 |
| | | | 606/169 |
| 2019/0142449 | A1 | 5/2019 | Shelton, IV et al. |
| 2019/0150712 | A1 | 5/2019 | Lin et al. |
| 2019/0282269 | A1 | 9/2019 | Adams et al. |

OTHER PUBLICATIONS

"Surgical laparoscopic serrated curved scissors," MediSimulator, date found via Google as Jan. 2017, URL: https://medisimulator. com/product/laparoscopic-curved-forceps-o5x330mm-360-rotation/.

* cited by examiner

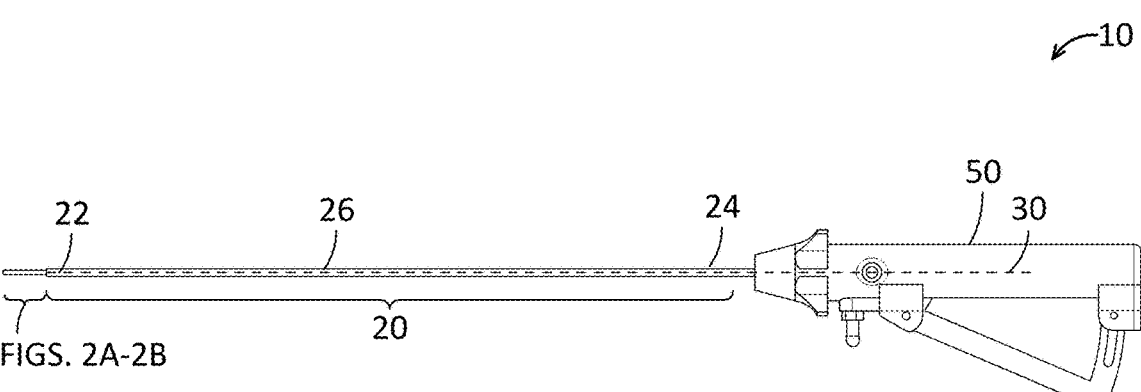
FIG. 1
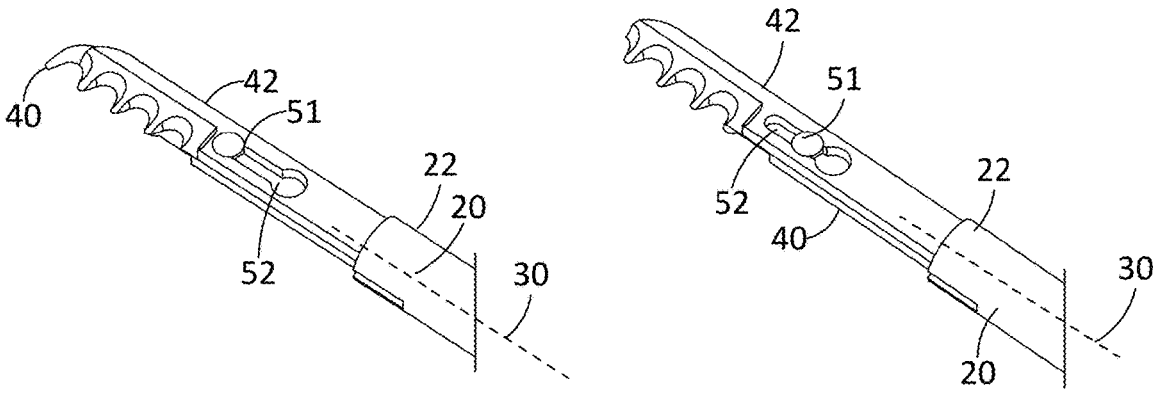
FIG. 2A                    FIG. 2B

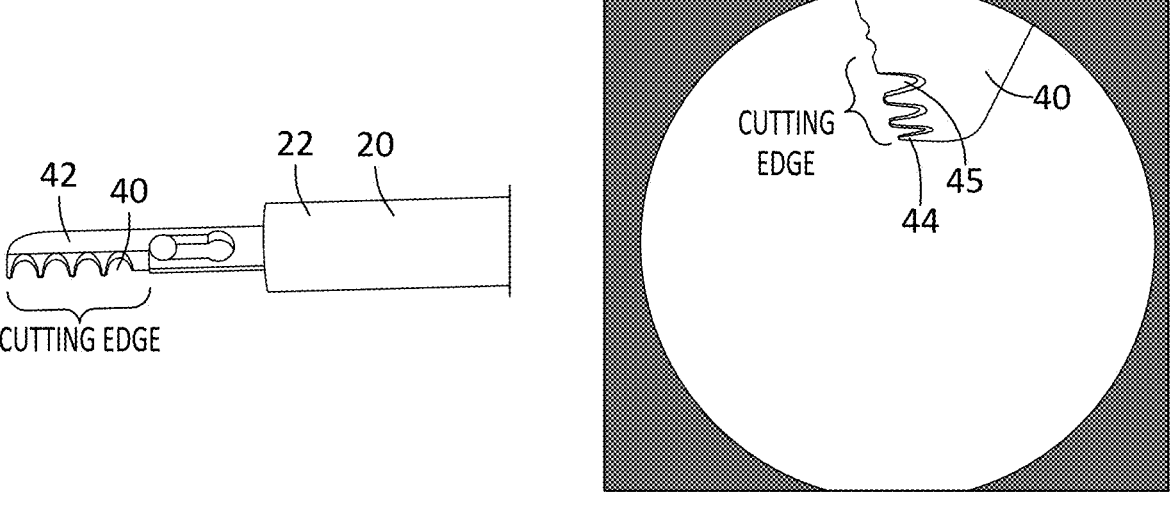
FIG. 7
FIG. 8
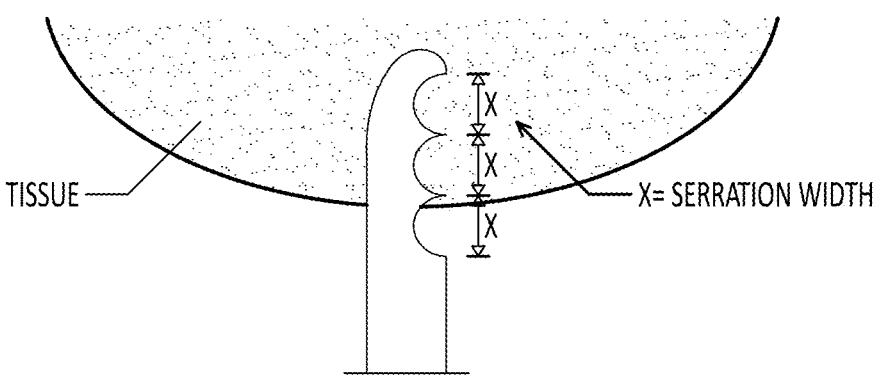
FIG. 9

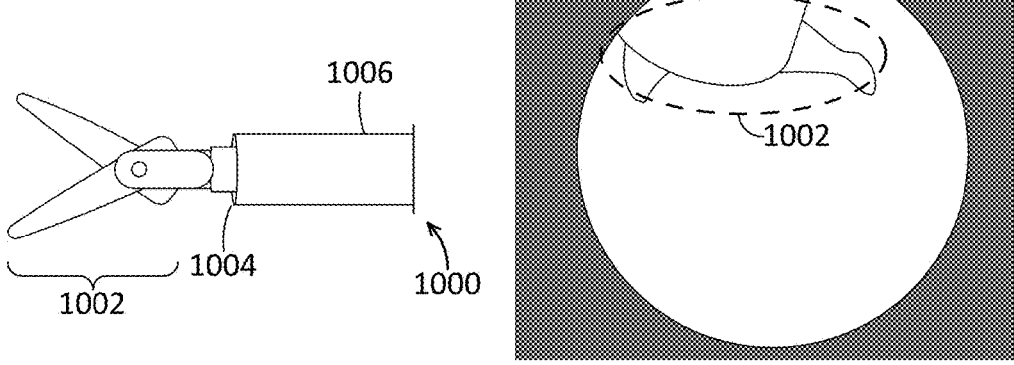
FIG. 10                          FIG. 11
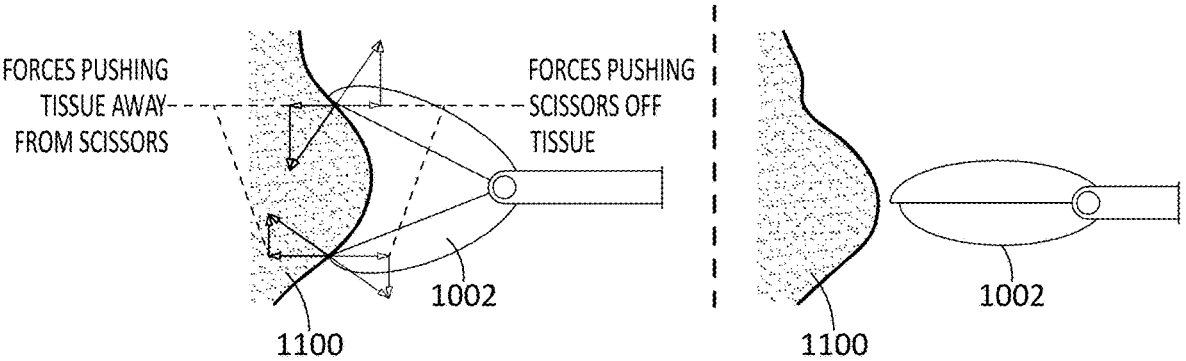
FIG. 12

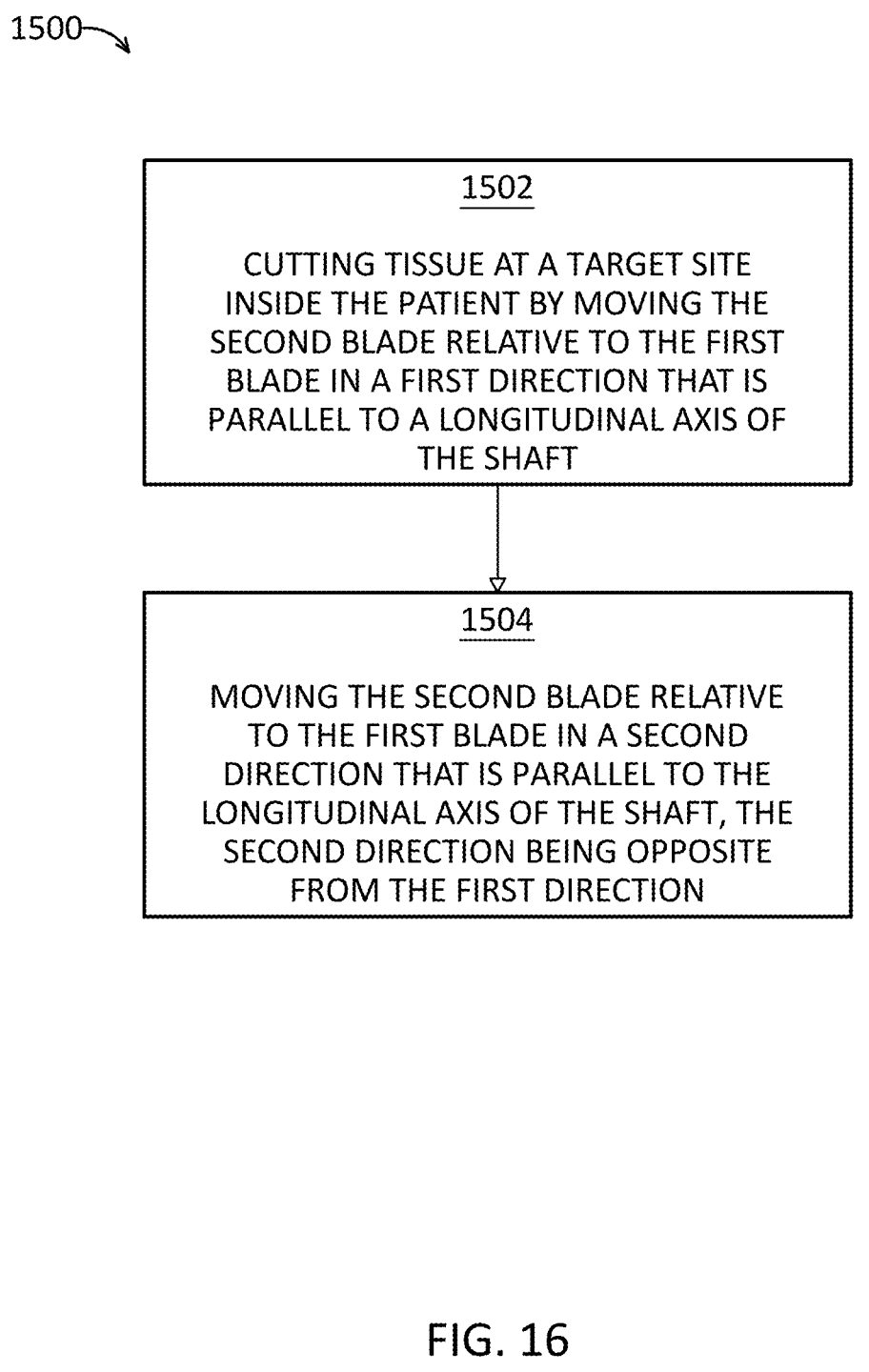

1500

1502

CUTTING TISSUE AT A TARGET SITE
INSIDE THE PATIENT BY MOVING THE
SECOND BLADE RELATIVE TO THE FIRST
BLADE IN A FIRST DIRECTION THAT IS
PARALLEL TO A LONGITUDINAL AXIS OF
THE SHAFT

1504

MOVING THE SECOND BLADE RELATIVE
TO THE FIRST BLADE IN A SECOND
DIRECTION THAT IS PARALLEL TO THE
LONGITUDINAL AXIS OF THE SHAFT, THE
SECOND DIRECTION BEING OPPOSITE
FROM THE FIRST DIRECTION

FIG. 16

RECIPROCATING SERRATED BLADE FOR PRECISION DISSECTION

RELATED APPLICATION DATA

This application is a continuation of International Patent Application No. PCT/US2020/055928 filed on Oct. 16, 2020, which claims priority to, and the benefit of, U.S. Provisional Patent Application No. 62/931,665 filed on Nov. 6, 2019. The entire disclosures of the above applications are expressly incorporated by reference herein.

FIELD

The field of the application relates to medical devices and methods for cutting tissue.

BACKGROUND

Medical devices have been used to cut tissues inside patients. For example, scissors and radio-frequency (RF) cutters have been used to cut tissues in target sites. However, these types of medical cutters have a few shortcomings.

For example, scissors may not be able to grasp tissues, and tissues temporarily held between the scissors may slide off during use of the scissors. Also, scissors may not be able to perform fine dissection of tissues in controlled manner due to the long continuous blades of the scissors.

RF cutters with elongated electrodes may also be undesirable for performing fine tissue dissections. Certain RF cutters may have an electrode tip for delivering cutting energy. However, such electrode tip may not be visible from a camera's point-of-view during cutting of the tissue. In addition, with this type of RF cutting device, the user may not be able to tell how much tissue is being cut.

New devices and methods for cutting tissues inside patients would be desirable.

SUMMARY

A medical device includes: a shaft having a distal end, a proximal end, and a shaft body extending between the distal end and the proximal end, the shaft body having a longitudinal axis; a first blade fixedly coupled to the distal end of the shaft, wherein the first blade has a first rectilinear planar surface; a second blade in contact with the first blade, wherein the second blade has a second rectilinear planar surface, and wherein the second blade is configured to move in a reciprocating manner in opposite directions that are parallel to the longitudinal axis of the shaft body; and a handle coupled to the proximal end of the shaft; wherein the shaft, the first blade, and the second blade are sized for insertion into a patient.

Optionally, the shaft comprises a first elongated member and a second elongated member, wherein the first blade is fixedly coupled to the first elongated member, and wherein the second blade is fixedly coupled to the second elongated member, and wherein the second elongated member is moveable along the longitudinal axis relative to the first elongated member.

Optionally, the first elongated member comprises an outer tube, and the second elongated member comprises an inner elongated member disposed inside the outer tube.

Optionally, the second elongated member comprises a proximal member end, and a spherical connector at, or coupled to, the proximal member end.

Optionally, the handle comprises a user control mechanically coupled to the spherical connector.

Optionally, the spherical connector is configured to allow the user control to actuate the second blade while also allowing the second elongated member to rotate about the longitudinal axis relative to the user control.

Optionally, the medical device further includes a spring coupled to the second elongated member, wherein the spring is configured to apply a spring force in a direction that is opposite to a movement direction of the second elongated member.

Optionally, one of the first blade and the second blade comprises a protrusion, and another one of the first blade and the second blade comprises a slot for moveably accommodating the protrusion.

Optionally, the first blade comprises a serrated cutting edge.

Optionally, the second blade comprises a serrated cutting edge.

Optionally, the first blade comprises a plurality of indicators for indicating different respective degrees of tissue-penetration.

Optionally, the handle comprises a knob configured to rotate the shaft about the longitudinal axis.

Optionally, the knob is rotatable about the longitudinal axis.

Optionally, the handle comprises a user control configured to move the second blade.

Optionally, the user control comprises a pump trigger.

Optionally, the user control is moveable in a first actuation direction in response to pressure applied at the user control by a user, and is moveable in a second direction that is opposite to the first actuation direction in response to the user releasing the pressure applied at the user control.

Optionally, the user control is configured to move the second blade back-and-forth once in response to each instance of pressure applied at the user control followed by a release of the applied pressure.

Optionally, the user control is configured to move the second blade back-and-forth multiple times in response to each instance of pressure applied at the user control followed by a release of the applied pressure.

Optionally, the handle comprises a port in fluid communication with the distal end of the shaft.

Optionally, the shaft, the first blade, and the second blade are sized for insertion into a uterus. For example, the first and second blades may be inserted directly into the uterus, or may be inserted into the uterus via a hysteroscope.

Optionally, the medical device further includes a camera configured to view the first blade and an environment around the first blade.

Optionally, the medical device further includes a light source configured to illuminate an area around the first blade and/or the second blade.

Optionally, the medical device further includes a motor for actuating the second blade.

Optionally, the medical device further includes a cam with an asymmetric configuration, wherein the motor is configured to rotate the cam.

A method performed by a medical device, the medical device having a shaft, a first blade, and a second blade that is in contact with the first blade, wherein the first blade is fixedly coupled to a distal end of the shaft, wherein the shaft, the first blade, and the second blade are sized for insertion into a patient, wherein the first blade has a first rectilinear planar surface, and wherein the second blade has a second rectilinear planar surface, includes: cutting tissue at a target site inside the patient by moving the second blade relative to the first blade in a first direction that is parallel to a longitudinal axis of the shaft; and moving the second blade relative to the first blade in a second direction that is parallel to the longitudinal axis of the shaft, the second direction being opposite from the first direction.

Optionally, the first blade is fixedly coupled to a first elongated member, and the second blade is fixedly coupled to a second elongated member, and wherein the moving of the second blade in the first direction is caused by a movement of the second elongated member relative to the first elongated member.

Optionally, the first elongated member comprises an outer tube, and the second elongated member comprises an inner elongated member disposed inside the outer tube.

Optionally, the second elongated member comprises a proximal member end, and a spherical connector at, or coupled to, the proximal member end.

Optionally, the medical device also comprises a handle with a user control mechanically coupled to the spherical connector, and wherein a movement of the second blade in the first direction and/or the second direction is in response to an actuation of the user control.

Optionally, the spherical connector is configured to allow the user control to actuate the second blade while also allowing the second elongated member to rotate about the longitudinal axis relative to the user control.

Optionally, the method further includes providing a spring force by a spring in a direction that is opposite to a movement direction of the second elongated member.

Optionally, the method further includes guiding a movement of the second blade relative to the first blade, wherein the act of guiding is performed by a protrusion at one of the first blade and the second blade, the protrusion being accommodated in a slot at another one of the first blade and the second blade.

Optionally, the tissue is cut by a serrated cutting edge of the first blade.

Optionally, the tissue is cut by a serrated cutting edge of the second blade.

Optionally, the method further includes providing, by the first blade, a plurality of indicators for indicating different respective degrees of tissue-penetration.

Optionally, the method further includes changing an orientation of the first blade and the second blade, by a rotation of the shaft about the longitudinal axis.

Optionally, the medical device comprises a knob that is rotatable about the longitudinal axis, the knob configured to rotate the shaft about the longitudinal axis.

Optionally, a movement of the second blade in the first direction and/or the second direction is provisioned by a user control at a handle of the medical device.

Optionally, the user control comprises a pump trigger.

Optionally, the user control is moveable in a first actuation direction in response to pressure applied at the user control by a user, and is moveable in a second direction that is opposite to the first actuation direction in response to the user releasing the pressure applied at the user control.

Optionally, the second blade is moved back-and-forth once in response to each instance of pressure applied at the user control followed by a release of the applied pressure.

Optionally, the second blade is moved back-and-forth multiple times in response to each instance of pressure applied at the user control followed by a release of the applied pressure.

Optionally, the method further includes delivering fluid from the distal end of the shaft to a proximal end of the shaft.

Optionally, the act of cutting the tissue is performed inside a uterus.

Optionally, the method further includes: illuminating the target site inside the patient; and imaging, by a camera, the first blade and an environment around the first blade.

Optionally, the act of illuminating is performed by a light source.

Optionally, a movement of the second blade in the first direction and/or the second direction is caused by a motor.

Optionally, the method further includes rotating a cam, by the motor, wherein the cam has an asymmetric configuration.

A surgical device for cutting tissue, includes: a handle; a shaft coupled to a distal portion of the handle; a planar stationary cutting instrument fixedly coupled to a distal portion of the shaft, wherein the stationary cutting instrument has a first cutting edge on one side thereof; a planar moveable cutting instrument slideably coupled to the distal portion of the shaft, wherein the moveable cutting instrument has a second cutting edge on one side thereof, and wherein the first cutting edge and second cutting edge face the same direction; and a drive coupled to the moveable cutting instrument to translate and reciprocate the moveable cutting instrument relative to the stationary cutting instrument in response to a force applied to the drive and to cut tissue during translation and reciprocation of the moveable cutting instrument.

Optionally, the shaft comprises a first elongated member and a second elongated member, wherein the stationary cutting instrument is fixedly coupled to the first elongated member, and wherein the moveable cutting instrument is fixedly coupled to the second elongated member, and wherein the second elongated member is moveable along a longitudinal axis of the shaft relative to the first elongated member.

Optionally, the first elongated member comprises an outer tube, and the second elongated member comprises an inner elongated member disposed inside the outer tube.

Optionally, the second elongated member comprises a proximal member end, and a spherical connector at, or coupled to, the proximal member end.

Optionally, the handle comprises a user control mechanically coupled to the spherical connector.

Optionally, the spherical connector is configured to allow the user control to actuate the moveable cutting instrument while also allowing the second elongated member to rotate about the longitudinal axis relative to the user control.

Optionally, the surgical device further includes a spring coupled to the second elongated member, wherein the spring is configured to apply a spring force in a direction that is opposite to a movement direction of the second elongated member.

Optionally, one of the stationary cutting instrument and the moveable cutting instrument comprises a protrusion, and another one of the stationary cutting instrument and the moveable cutting instrument comprises a slot for moveably accommodating the protrusion.

Optionally, the first cutting edge comprises a serrated cutting edge.

Optionally, the second cutting edge comprises a serrated cutting edge.

Optionally, the stationary cutting instrument comprises a plurality of indicators for indicating different respective degrees of tissue-penetration.

Optionally, the handle comprises a knob configured to rotate the shaft about a longitudinal axis of the shaft.

Optionally, the knob is rotatable about the longitudinal axis of the shaft.

Optionally, the handle comprises a user control configured to move the moveable cutting instrument.

Optionally, the user control comprises a pump trigger.

Optionally, the user control is moveable in a first actuation direction in response to pressure applied at the user control by a user, and is moveable in a second direction that is opposite to the first actuation direction in response to the user releasing the pressure applied at the user control.

Optionally, the user control is configured to move the moveable cutting instrument back-and-forth once in response to each instance of pressure applied at the user control followed by a release of the applied pressure.

Optionally, the user control is configured to move the moveable cutting instrument back-and-forth multiple times in response to each instance of pressure applied at the user control followed by a release of the applied pressure.

Optionally, the handle comprises a port in fluid communication with a distal end of the shaft.

Optionally, the shaft, the stationary cutting instrument, and the moveable cutting instrument are sized for insertion into a uterus.

Optionally, the surgical device further includes a camera configured to view the stationary cutting instrument and an environment around the stationary cutting instrument.

Optionally, the surgical device further includes a light source configured to illuminate an area around the stationary cutting instrument and/or the moveable cutting instrument.

Optionally, the surgical device further includes a motor for actuating the moveable cutting instrument.

Optionally, the surgical device further includes a cam with an asymmetric configuration, wherein the motor is configured to rotate the cam.

A method for cutting tissue, includes: inserting a distal portion of a surgical device tangentially against targeted tissue, the surgical instrument having a first planar cutting member and a second planar cutting member, the first planar cutting member having a first cutting edge, the second planar cutting member having a second cutting edge; translating the second planar cutting member relative to the first planar cutting member, wherein during the act of translating, the first cutting edge and the second cutting edge shear the targeted tissue; and reciprocating the second planar cutting member relative to the first planar cutting member.

Optionally, the first planar cutting member is fixedly coupled to a first elongated member, and the second planar cutting member is fixedly coupled to a second elongated member, and wherein the translating of the second planar cutting member is caused by a movement of the second elongated member relative to the first elongated member.

Optionally, the first elongated member comprises an outer tube, and the second elongated member comprises an inner elongated member disposed inside the outer tube.

Optionally, the second elongated member comprises a proximal member end, and a spherical connector at, or coupled to, the proximal member end.

Optionally, the surgical device also comprises a handle with a user control mechanically coupled to the spherical connector, and wherein a translational movement of the second planar cutting member is in response to an actuation of the user control.

Optionally, the spherical connector is configured to allow the user control to actuate the second planar cutting member while also allowing the second elongated member to rotate about a longitudinal axis of the first elongated member relative to the user control.

Optionally, the method further includes providing a spring force by a spring in a direction that is opposite to a movement direction of the second planar cutting member.

Optionally, the method further includes guiding a movement of the second planar cutting member relative to the first planar cutting member, wherein the act of guiding is performed by a protrusion at one of the first planar cutting member and the second planar cutting member, the protrusion being accommodated in a slot at another one of the first planar cutting member and the second planar cutting member.

Optionally, the first cutting edge comprises a serrated cutting edge.

Optionally, the second cutting edge comprises a serrated cutting edge.

Optionally, the method further includes providing, by the first planar cutting member, a plurality of indicators for indicating different respective degrees of tissue-penetration.

Optionally, the method further includes changing an orientation of the first planar cutting member and the second planar cutting member, by a rotation of a shaft about a longitudinal axis of the shaft.

Optionally, the surgical device comprises a knob that is rotatable about the longitudinal axis of the shaft, the knob configured to rotate the shaft about the longitudinal axis.

Optionally, a movement of the second planar cutting member is provisioned by a user control at a handle of the surgical device.

Optionally, the user control comprises a pump trigger.

Optionally, the user control is moveable in a first actuation direction in response to pressure applied at the user control by a user, and is moveable in a second direction that is opposite to the first actuation direction in response to the user releasing the pressure applied at the user control.

Optionally, the second planar cutting member is moved back-and-forth once in response to each instance of pressure applied at the user control followed by a release of the applied pressure.

Optionally, the second planar cutting member is moved back-and-forth multiple times in response to each instance of pressure applied at the user control followed by a release of the applied pressure.

Optionally, the method further includes delivering fluid from a distal end of the surgical device to a proximal end of the surgical device.

Optionally, the targeted tissue is inside a uterus.

Optionally, the method further includes: illuminating targeted tissue; and imaging, by a camera, the first planar cutting member and an environment around the first planar cutting member.

Optionally, the act of illuminating is performed by a light source.

Optionally, a movement of the second planar cutting member is caused by a motor.

Optionally, the method further includes rotating a cam, by the motor, wherein the cam has an asymmetric configuration.

Other and further aspects and features will be evident from reading the following detailed description in view of the accompanying drawings.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the aboverecited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 1 illustrates a medical device for cutting tissue.

FIGS. 2A-2B illustrate a first blade and a second blade at a distal end of the medical device of FIG. 1.

FIG. 7 illustrates a prototype of the medical device of FIG. 1.

FIG. 8 illustrates the cutting edge of the medical device of FIG. 7 from a camera's point-of-view during a medical procedure.

FIG. 9 illustrates a technique of determining a degree of tissue penetration.

FIG. 10 illustrates a tissue cutter in a form of scissors.

FIG. 11 illustrates the scissors of FIG. 10 as viewed by a camera during a medical procedure.

FIG. 12 illustrates slippage of tissue away from scissors.

FIG. 16 illustrates a method of cutting tissue.

DETAILED DESCRIPTION

Figure 3:
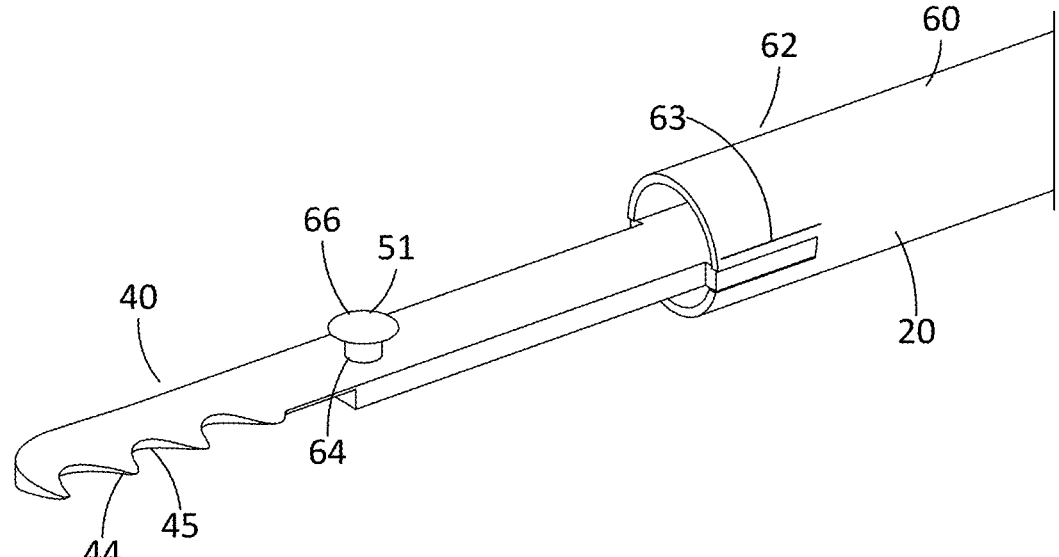
FIG. 3 illustrates the first blade of the medical device of FIG. 1.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments, and are not intended as an exhaustive depiction or limitation on the scope of the claimed invention. In addition, each of the illustrated embodiments does not necessarily depict all of the aspects or advantages of the respective embodiment. Further, an aspect or an advantage described in conjunction with a particular embodiment is not necessarily limited to that embodiment and can be practiced in any other embodiments even if not so illustrated, or if not so explicitly described.

FIGS. 1-2 illustrate a medical device 10 for cutting tissue. As shown in FIG. 1, the medical device 10 includes a shaft 20 having a distal end 22, a proximal end 24, and a shaft body 26 extending between the distal end 22 and the proximal end 24, the shaft body 26 having a longitudinal axis 30. As shown in FIGS. 2A-2B, the medical device 10 also includes a first blade 40 fixedly coupled to the distal end 22 of the shaft 20, and a second blade 42 in contact with the first blade 40. The second blade 42 is configured to move in a reciprocating manner in opposite directions that are parallel to the longitudinal axis 30 of the shaft body 26. As shown in FIG. 1, the medical device 10 also includes a handle 50 coupled to the proximal end 24 of the shaft 20.

The shaft 20, the first blade 40, and the second blade 42 are sized for insertion into a patient through a natural opening or an incision.

As shown in FIG. 2A, the first blade 40 has a protrusion 51 configured (e.g., sized and/or shaped) for placement in a slot 52 at the second blade 42. The slot 52 guides the protrusion 51 to thereby define a direction and range of motion that the second blade 42 can translate with respect to the first blade 40. As shown in the figure, the slot 52 extends in a direction that is parallel to the longitudinal axis 30 of the shaft 20. Accordingly, the direction of translation of the second blade 42 relative to the first blade 40 is also parallel to the longitudinal axis 30 of the shaft 20. FIG. 2B illustrates the second blade 42 in a more distal position relative to the first blade 40 as compared to FIG. 2A.

Figure 4:
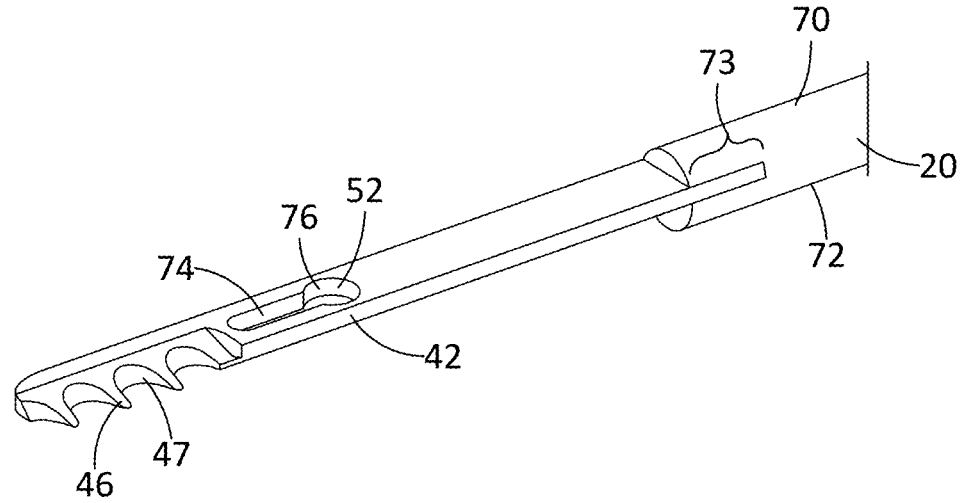
FIG. 4 illustrates the second blade of the medical device of FIG. 1.
Figure 5:
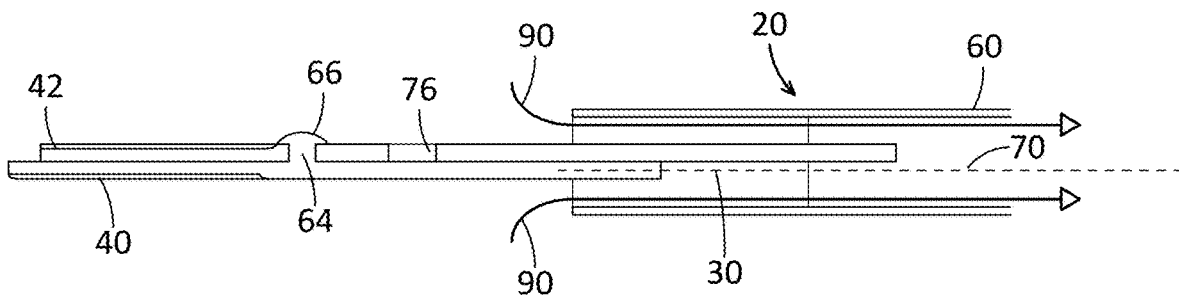
FIG. 5 illustrates the first blade and the second blade of the medical device of FIG. 1, particularly showing the first blade and the second blade coupled to respective elongated members.

FIGS. 3-5 illustrate the distal end of the medical device 10 of FIG. 1 in further detail. As shown in FIG. 3, the shaft 20 comprises a first elongated member 60. A proximal end of the first blade 40 is placed in a slot at a distal end 62 of the first elongated member 60, and the proximal end of the first blade 40 is secured to the distal end 62 of the first elongated member 60 via a weld 63. In the illustrated example, the first elongated member 60 to which the first blade 40 is secured is in a form of an outer tube. In other embodiments, the first elongated member 60 may be an inner elongated member that is positioned inside an outer tube. Also, in other embodiments, instead of using the weld 63, the proximal end of the first blade 40 may be secured to the first elongated member 60 using other mechanisms, such as glue, fusion, mechanical connector, etc. As shown in FIG. 3, the protrusion 51 at the first blade 40 has a protrusion shaft 64 and a protrusion cap 66. The protrusion shaft 64 is configured for placement into the slot 52 of the second blade 42 (shown in FIG. 4). The protrusion cap 66 has a larger cross-sectional dimension compared to that of the protrusion shaft 64.

As shown in FIG. 4, the shaft 20 of the medical device 10 also has a second elongated member 70 with a distal end 72. A proximal end of the second blade 42 is secured to the distal end 72 of the second elongated member 70 via a weld 73. In the illustrated example, the second elongated member 70 to which the second blade 42 is secured is an inner elongated member that is configured (e.g., sized and/or shaped) for placement inside the first elongated member 60. In other embodiments, the second elongated member 70 may be an outer tube. Also, in other embodiments, instead of using the weld 73, the proximal end of the second blade 42 may be secured to the second elongated member 70 using other mechanisms, such as glue, fusion, mechanical connector, etc. As shown in the figure, the slot 52 has an elongated slot portion 74 and an enlarged opening 76. The enlarged opening 76 is configured to accommodate the protrusion cap 66 (shown in FIG. 3) at the first blade 40, so that the protrusion cap 66 can be inserted through the enlarged opening 76. The elongated slot portion 74 is configured (e.g., sized and/or shaped) to accommodate the protrusion shaft 64 (shown in FIG. 3) at the first blade 40, and to allow the protrusion shaft 64 to slide therein.

As shown in FIGS. 3-4, each of the first blade 40 and the second blade 42 comprises a serrated cutting edge. In particular, the cutting edge of the first blade 40 has a plurality of peaks 44 and a plurality of recesses 45. This creates a cutting edge for the first blade 40 with serrations. Similarly, the cutting edge of the second blade 42 has a plurality of peaks 46 and a plurality of recesses 47. This creates a cutting edge for the second blade 42 with serrations. In some embodiments, the serrations at the first blade 40 and/or the second blade 42 may function as a plurality of indicators for indicating different respective degrees of tissue-penetration by the first blade 40 and/or the second blade 42. This feature will be further described below with reference to FIGS. 7-9.

FIG. 5 illustrates the first blade 40 and the second blade 42 of the medical device 10 of FIG. 1, particularly showing the first blade 40 and the second blade 42 coupled respectively to the first elongated member 60 and the second elongated member 70. As shown in the figure, the first blade 40 is coupled to the first elongated member 60, and the second blade 42 is coupled to the second elongated member 70. The first elongated member 60 is an outer tube in the example, and the second elongated member 70 is an inner elongated member that is configured to slide within the outer tube. The first elongated member 60 and the second elongated member 70 together form the shaft 20 of the medical device 10. In other embodiments, the first elongated member 60 itself may constitute the shaft 20 of the medical device 10. In such cases, the second elongated member 70 may be considered to be an inner member that is configured to slide within the shaft 20 of the medical device 10.

As shown in FIG. 5, after the protrusion cap 66 has been inserted through the enlarged opening 76, the first blade 40 and the second blade 42 are then in abutment against each other. The protrusion shaft 64 may then be moved into the elongated slot 74 (shown in FIG. 4). The elongated slot 74 and the protrusion shaft 64 guide the translational movement of the second blade 42 relative to the first blade 40, so that the second blade 42 moves in a direction that is parallel to the longitudinal axis 30 of the shaft 20. While the second blade 42 translates relative to the first blade 40, the protrusion cap 66 keeps the first blade 40 and the second blade 42 in close contact with each other. As shown in the figure, the first blade 40 has a first rectilinear planar surface, and the second blade 42 has a second rectilinear planar surface. The planar surfaces allow the second blade 42 to translate relative to the first blade 40 smoothly while in abutment with the first blade 40. Also, as shown in FIG. 5, in some embodiments, the first elongated member 60 and/or the second elongated member 70 may optionally include one or more channels configured to allow transport of fluid 90 from the distal end to the proximal end of the shaft 20, and/or from the proximal end of the shaft 20 to the distal end of the shaft 20.

Figure 6:
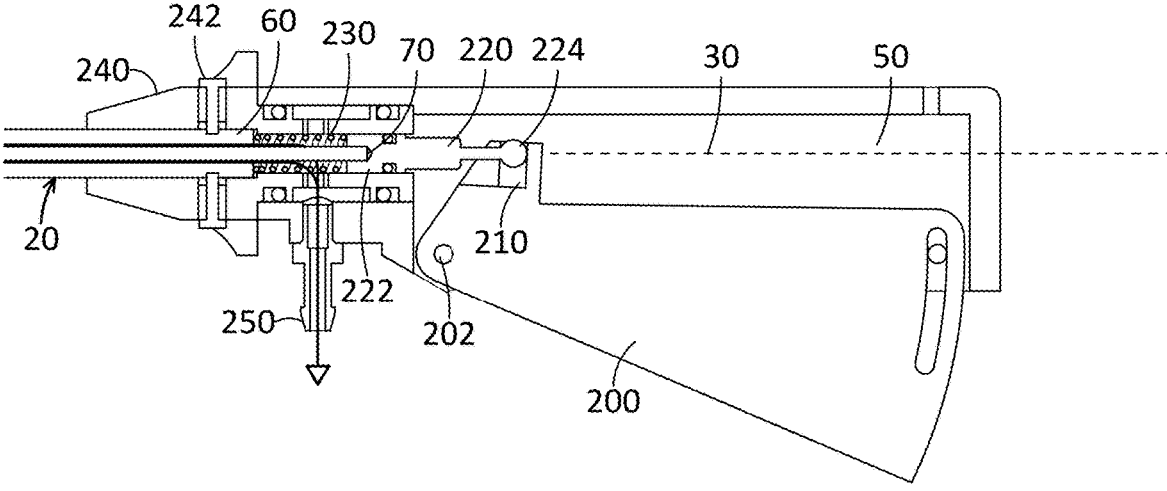
FIG. 6 illustrates a partial cross-sectional view of the medical device of FIG. 1.

FIG. 6 illustrates a partial cross-sectional view of the medical device 10 of FIG. 1. As shown in the figure, the handle 50 of the medical device 10 includes a user control 200 configured to move the second elongated member 70 to which the second blade 42 is attached. In the illustrated example, the user control 200 comprises a pump trigger that is manually operated. In other embodiments, the user control 200 may have other configurations. The user control 200 is rotatably coupled to a part of the handle 50 via a hinge 202, which allows the user control 200 to rotate about an axis of the hinge 202 in response to a user squeezing the user control 200 on the handle 50. The user control 200 is moveable in a first actuation direction in response to pressure applied at the user control 200 by a user, and is moveable in a second direction that is opposite to the first actuation direction in response to the user releasing the pressure applied at the user control 200. In some embodiments, the user control 200 is configured to move the second blade 42 back-and-forth once in response to each instance of pressure applied at the user control 200 followed by a release of the applied pressure. In other embodiments, the user control 200 is configured to move the second blade 42 back-and-forth multiple times in response to each instance of pressure applied at the user control 200 followed by a release of the applied pressure.

As shown in FIG. 6, the proximal end of the second elongated member 70 is coupled to a distal end of a linkage 220. The linkage 220 includes a proximal end with a spherical connector 224. The linkage 220 is fixedly coupled (e.g., via a weld, adhesive, connector, etc.) to the second elongated member 70. Thus, the spherical connector 224 is coupled to the proximal end of the second elongated member 70 via the body of the linkage 220. In other embodiments, the linkage 220 may be integrally formed with the second elongated member 70. The user control 200 includes a socket 210 configured to receive the spherical connector 224. The spherical connector 224 is configured to allow the user control 200 to actuate the second blade 42 while also allowing the second elongated member 70 to rotate about the longitudinal axis 30 relative to the user control 200. In particular, pressing the user control 200 at the handle 50 will cause the user control 200 to rotate about the hinge 202, thereby moving the socket 210 and the spherical connector 224 therein distally. This, in turn, causes the linkage 220 (and the second elongated member 70 and the second blade 42 attached thereto) to move distally.

The handle 50 also comprises a knob 240 configured to rotate both the first and second elongated members 60, 70 of the shaft 20 simultaneously about the longitudinal axis 30 of the shaft 20. In the illustrated embodiments, the knob 240 is located at a distal end of the handle 50 and is rotatable about the longitudinal axis 30. In other embodiments, the knob 240 may be located at other parts of the handle 50. Also, in other embodiments, the knob 240 may be rotatable about other axes that are different from the longitudinal axis 30. As shown in the figure, the knob 240 is fixedly secured to the first elongated member 60 via one or more screws 242. This allows the first elongated member 60 to rotate about the longitudinal axis 30 in response to a turning of the knob 240 about the longitudinal axis 30. Since the second elongated member 70 is coupled to the first elongated member 60 via the connection (i.e., the protrusion shaft 64 and the protrusion cap 66) connecting the first and second blades 40, 42, the turning of the first elongated member 60 will also cause the second elongated member 70 to turn simultaneously. In other embodiments, instead of using one or more screws 242 to fixedly connect the knob 240 to the first elongated member 60, other types of connection, such as a weld, an adhesive, fusion, mechanical connector, etc., may be used.

It should be noted that the spherical connector 224 is advantageous because it allows the second elongated member 70 to rotate about the longitudinal axis 30, and regardless of the angular position of the second elongated member 70 with respect to the longitudinal axis 30, the spherical connector 224 also allows the user control 200 to distally advance the second elongated member 70 in response to actuation of the user control 200.

As shown in FIG. 6, the medical device 10 also includes a spring 230 coupled to the second elongated member 70. The spring 230 is configured to apply a spring force in a direction that is opposite to a movement direction of the second elongated member 70. In the illustrated embodiments, the spring 230 is disposed around the second elongated member 70 and is located between the proximal end of the first elongated member 60 and the distal end of the linkage 220. Accordingly, when the linkage 220 is advanced distally by the user control 200 to move the second elongated member 70 distally, the spring 230 will be compressed between the distal end of the linkage 220 and the proximal end of the first elongated member 60. When the user control 200 is released, the spring force provided by the spring 230 will push the linkage 220 (and hence, the second elongated member 70) proximally. Therefore, pressing and releasing the user control 200 will cause the second elongated member 70 to move back-and-forth relative to the first elongated member 60 in directions that are parallel to the longitudinal axis 30 of the shaft 20. This, in turn, will cause the second blade 42 to move back-and-forth relative to the first blade 40 in directions that are also parallel to the longitudinal axis 30 of the shaft 20.

The handle further includes a port 250 in fluid communication with the distal end of the shaft 20 via an opening at the proximal end of the shaft 20. The port 250 may be configured to suction fluid at the distal end of the shaft 20. Alternatively, or additionally, the port 250 may be configured to deliver fluid (e.g., saline, drug, etc.) to the distal end of the shaft 20.

In some embodiments, the medical device 10 may optionally further include a camera configured to view the first blade 40 and/or the second blade 42, and an environment around the first blade 40 and/or the second blade 42. The camera may be coupled outside the shaft 20. Alternatively, the camera may be housed within a separate channel inside the shaft 20 or outside the shaft 20. In further embodiments, the camera may be separate from the medical device 10 in the sense that the medical device 10 may be advanced through the working channel of an endoscope.

Also, in some embodiments, the medical device 10 may optionally further include a light source configured to illuminate an area around the first blade 40 and/or the second blade 42. The light source may be located at the medical device 10, such as at the distal 22 end of the shaft 20. Alternatively, the light source may be located at a proximal end of the medical device 10, such as at the handle 50. In such cases, the light provided by the light source may be transmitted via fiber optics to the distal end of the medical device 10.

Furthermore, in some embodiments, the shaft 20, the first blade 40, and the second blade 42 may be sized for insertion into a uterus. This allows the medical device 10 to cut tissue inside the uterus. In one implementation, the medical device 10 may be implemented as a hysteroscopic tool. In such cases, the medical device 10 may be used for fine dissection of pseudo-capsule and connective tissue inside the uterus, which can help release and enucleate deeply embedded fibroids. The fine dissection may also be used to cut away septum and adhesions found in uterus.

In other embodiments, the shaft 20, the first blade 40, and the second blade 42 may be sized for insertion into other parts of the patient via a small incision. The medical device 10 may be configured to cut tissues in other parts of the body in other embodiments.

In addition, in medical device 10 may be implemented as a disposable device. This has the advantage that each medical device 10 provides new blades 40, 42 with sharp edges every time. In other embodiments, the medical device 10, or parts of the medical device 10, may be re-usable. For example, in other embodiments, the blades 40, 42 may be removably attachable to the respective elongated members 60, 70. In such cases, after the blades 40, 42 are used, they may be detached from the respective elongated members 60, 70. Then new blades may be removably attached to the respective elongated members 60, 70. This allows parts of the medical device 10 to be re-used to treat different patients.

FIG. 7 illustrates a prototype of the medical device 10 of FIG. 1. FIG. 8 illustrates the serrated cutting edge of the first blade 40 of the medical device 10 of FIG. 7 from a camera's point-of-view during a medical procedure. As shown in the figure, due to the first blade 40 having serrations, the serrations provide indicators informing a user of the medical device 10 how deep the blades 40, 42 have cut into the tissue. In some cases, the serrations of the first blade 40 may be configured to have a size and/or spacing (between adjacent serrations) that allow the user to clearly and easily determine the number serrations in a camera image. For example, in one implementation, the number of serrations on the first blade 40 may be eight or less, or six or less, or 5 or less, or 4 or less, or 3 or less, or 2 or less. If the number of serrations is high (e.g., more than 10) and/or if the serrations are too small in size (e.g., less than 0.5 mm), then the user may have a hard time counting the number of serrations during the medical procedure. In some embodiments, the serrations may have a serration width that is anywhere from 1 mm to 10 mm.

It should be noted that having the first blade 40 as a "stationary" blade that does not move relative to the shaft 20 is advantageous. This is because it allows the first blade 40 to be used as a "ruler" to measure a degree of tissue penetration by the blade 40 and/or the blade 42. As the second blade 42 moves in a reciprocating manner relative to the first blade 40 to cut tissue, the first blade 40 stays stationary relative to the shaft 20, thereby allowing the user to easily determine how deep the blades 40, 42 have cut into the tissue. In other embodiments, the serrations at the second blade 42 may also function as indicators for indicating a degree of tissue penetration by the blade 40 and/or the blade 42.

FIG. 9 illustrates a technique of determining a degree of tissue penetration using number of serrations on the blade 40/42. In the example, assuming the blade 40/42 has three serrations with width of serration=2 mm. In such cases, if the user can see only one serration from the camera image, then the tissue penetration may be calculated as (total number of serrations−serration(s) in image)*width of serration=(3−1)*2 mm=4 mm. Accordingly, the user can simply count the number of serrations (or teeth) in the camera image, and then can determine the tissue penetration based on the counted number of serrations.

The medical device 10 described herein is advantageous over tissue cutter having scissors. FIG. 10 illustrates a tissue cutter 1000 having scissors 1002 attached to a distal end 1004 of a shaft 1006. FIG. 11 illustrates the scissors 1002 of FIG. 10 as viewed by a camera during a medical procedure. As shown in the figure, the exact location where the scissors 1002 cut the tissue is hard to identify. The scissors 1002 are hard to visualize in a 0-degree scope because their cutting edges are not on the side, but at the distal most edge of the device. In addition, the scissors 1002 of the tissue cutter 1000 does not have any indicators for allowing the user to see how much tissue is being cut by the scissors 1002. Also, scissor cutting is an interrupted process involving opening the scissor blades, positioning the scissor blades, and then closing the scissor blades. The medical device 10 described herein is advantageous over the scissors 1002 because it provides a more continuous cutting process with more control. Also, the blade 40 and/or the blade 42 can be easier to visualize in a 0-degree scope. In addition, the indicators at the first blade 40 allow a user to easily determine a depth of cut.

Furthermore, the scissors 1002 may not be able to grasp tissue adequately, resulting in slippage of the tissue away from the scissors 1002. FIG. 12 illustrates slippage of tissue 1100 away from scissors 1002. As shown in the left diagram of FIG. 12, when attempting to grasp tissue 1100, the scissors 1002 initially engage the tissue 1100 at an angle. Due to such angle, the scissors 1002 may not have sufficient grip or traction against the tissue 1100, resulting in the tissue 1100 slipping away from the scissors 1002—like that shown in the right diagram of FIG. 12. The blades 40, 42 of the medical device 10 described herein are better than the scissors 1002 because they allow tissue to be trapped between the serrations, thereby avoiding or reducing risk of tissue slippage away from the cutting edge of the blades 40, 42.

Figures 13, 14:
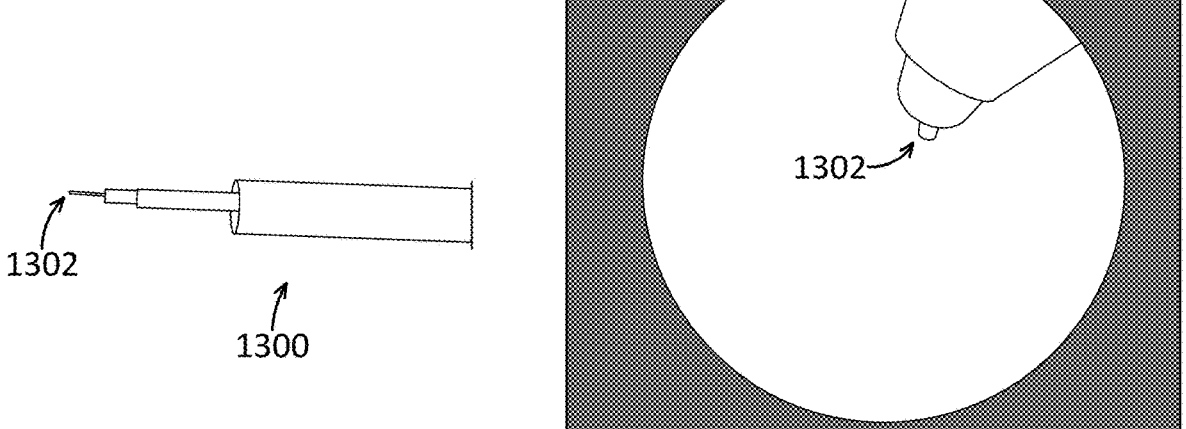
FIG. 13 illustrates a radio-frequency (RF) cutter.
FIG. 14 illustrates the RF cutter of FIG. 13 as viewed by a camera during a medical procedure.

It should be noted that the medical device 10 described herein is also advantageous over RF cutter. FIG. 13 illustrates a RF cutter 1300 having an electrode tip 1302. FIG. 14 illustrates the RF cutter 1300 of FIG. 13 as viewed by a camera during a medical procedure. As shown in the figure, the electrode tip 1302 is hard to see from the camera's point-of-view during the medical procedure. Also, due to the small profile of the electrode tip 1302, the exact location here the tissue is being cut by the electrode tip 1302 is not easy to identify. Furthermore, the RF cutter 1300 does not have any indicators for allowing the user to see how much tissue is being cut. In addition, RF cutter 1300 requires a RF generator to drive it, and a lot of skill to control the depth of cut in order to avoid thermal damage to surrounding tissue. The medical device 10 described herein does not require any RF generator, and does not create any risk of thermal damage to surrounding tissue. Also, the indicators at the first blade 40 allow a user to easily determine a depth of cut.

Figure 15:
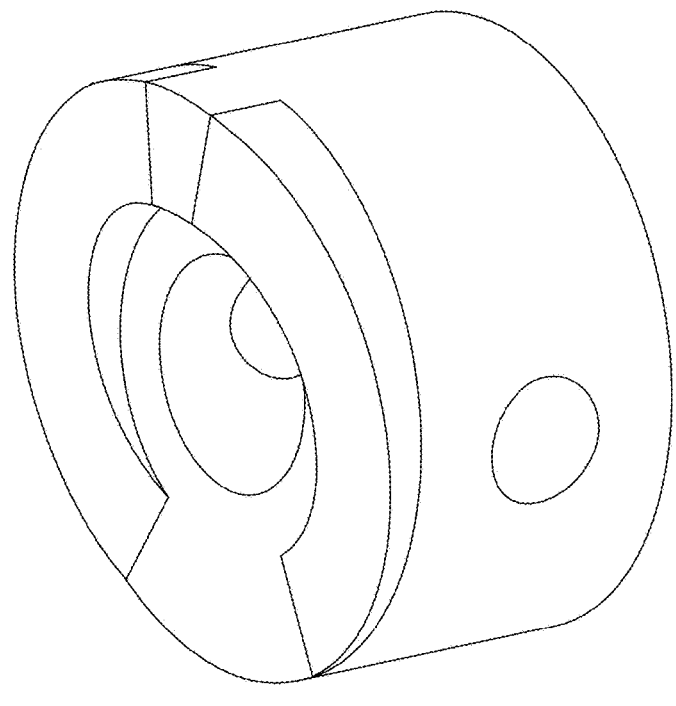
FIG. 15 illustrates an example of a cam that may be incorporated into a handle of the medical device of FIG. 1.

Although the medical device 10 has been described as being powered by the user, in other embodiments, the medical device 10 may optionally include a motor configured to actuate the second blade 42. The motor may be accommodated in a housing of the medical device 10 in some embodiments. In other embodiments, the motor may be external to the housing of the medical device 10. In such cases, the motor may transmit torque to a cam through a drive shaft (e.g., a flexible drive shaft). For example, the cam may have an asymmetric configuration (like that shown in FIG. 15) such that the cam is thicker on one side of a rotational axis than an opposite side. Accordingly, as the cam rotates, the proximal end of the second elongated member 70 (or the linkage 220 if one is provided) will alternately come into contact with the thicker side of the cam followed by the narrower side of the cam. The handle 50 may include a button for actuating the motor. In some cases, a single actuation of the button may cause the motor to rotate the cam once to thereby push the second blade 42 distally once. The second blade 42 will retract proximally automatically due to the spring 230. In other cases, a single actuation of the button may cause the motor to rotate the cam multiple times to thereby (1) push the second blade 42 distally and (2) allow the second blade 42 to retract, multiple times. The number of times may be pre-determined (e.g., pre-configured) so that after the number of pre-determined rotations have been reached, the motor will automatically stop rotating the cam. In some embodiments, the handle 50 may optionally further include an adjuster for allowing a user to adjust how many times the motor will move the second blade 42 in response to a single actuation of the button. In further embodiments, the motor may be configured to rotate the cam as long as the button is pressed, thereby causing the second blade 42 to move back-and-forth until the button is released. In such cases, the user can selectively determine how many times the second blade 42 will move back-and-forth while using the medical device 10.

FIG. 16 illustrates a method 1500 of cutting tissue performed by a medical device. In some embodiments, the medical device performing the method 1500 has a shaft, a first blade, and a second blade that is in contact with the first blade, wherein the first blade is fixedly coupled to a distal end of the shaft, wherein the shaft, the first blade, and the second blade are sized for insertion into a patient. The first blade may have a first rectilinear planar surface, and the second blade may have a second rectilinear planar surface. The method 1500 includes cutting tissue at a target site inside the patient by moving the second blade relative to the first blade in a first direction that is parallel to a longitudinal axis of the shaft (item 1502). The method 1500 also includes moving the second blade relative to the first blade in a second direction that is parallel to the longitudinal axis of the shaft, the second direction being opposite from the first direction (item 1504).

Optionally, in the method 1500, the first blade is fixedly coupled to a first elongated member, and the second blade is fixedly coupled to a second elongated member, and wherein the moving of the second blade in the first direction is caused by a movement of the second elongated member relative to the first elongated member.

Optionally, in the method 1500, the first elongated member comprises an outer tube, and the second elongated member comprises an inner elongated member disposed inside the outer tube.

Optionally, in the method 1500, the second elongated member comprises a proximal member end, and a spherical connector at, or coupled to, the proximal member end.

Optionally, in the method 1500, the medical device also comprises a handle with a user control mechanically coupled to the spherical connector, and wherein a movement of the second blade in the first direction and/or the second direction is in response to an actuation of the user control.

Optionally, in the method 1500, the spherical connector is configured to allow the user control to actuate the second blade while also allowing the second elongated member to rotate about the longitudinal axis relative to the user control.

Optionally, the method 1500 further includes providing a spring force by a spring in a direction that is opposite to a movement direction of the second elongated member.

Optionally, the method 1500 further includes guiding a movement of the second blade relative to the first blade, wherein the act of guiding is performed by a protrusion at one of the first blade and the second blade, the protrusion being accommodated in a slot at another one of the first blade and the second blade.

Optionally, in the method 1500, the tissue is cut by a serrated cutting edge of the first blade.

Optionally, in the method 1500, the tissue is cut by a serrated cutting edge of the second blade.

Optionally, the method 1500 further includes providing, by the first blade, a plurality of indicators for indicating different respective degrees of tissue-penetration.

Optionally, the method 1500 further includes changing an orientation of the first blade and the second blade, by a rotation of the shaft about the longitudinal axis.

Optionally, in the method 1500, the medical device comprises a knob that is rotatable about the longitudinal axis, the knob configured to rotate the shaft about the longitudinal axis.

Optionally, in the method 1500, a movement of the second blade in the first direction and/or the second direction is provisioned by a user control at a handle of the medical device.

Optionally, in the method 1500, the user control comprises a pump trigger.

Optionally, in the method 1500, the user control is moveable in a first actuation direction in response to pressure applied at the user control by a user, and is moveable in a second direction that is opposite to the first actuation direction in response to the user releasing the pressure applied at the user control.

Optionally, in the method 1500, the second blade is moved back-and-forth once in response to each instance of pressure applied at the user control followed by a release of the applied pressure.

Optionally, in the method 1500, the second blade is moved back-and-forth multiple times in response to each instance of pressure applied at the user control followed by a release of the applied pressure.

Optionally, the method 1500 further includes delivering fluid from the distal end of the shaft to a proximal end of the shaft.

Optionally, in the method 1500, the act of cutting the tissue is performed inside a uterus.

Optionally, the method 1500 further includes: illuminating the target site inside the patient; and imaging, by a camera, the first blade and an environment around the first blade.

Optionally, in the method 1500, the act of illuminating is performed by a light source.

Optionally, in the method 1500, a movement of the second blade in the first direction and/or the second direction is caused by a motor.

Optionally, the method 1500 further includes rotating a cam, by the motor, wherein the cam has an asymmetric configuration.

The following items are exemplary features of embodiments described herein. Each item may be an embodiment itself or may be a part of an embodiment. One or more items described below may be combined with other item(s) in an embodiment.

Item 1: A medical device includes: a shaft having a distal end, a proximal end, and a shaft body extending between the distal end and the proximal end, the shaft body having a longitudinal axis; a first blade fixedly coupled to the distal end of the shaft, wherein the first blade has a first rectilinear planar surface; a second blade in contact with the first blade, wherein the second blade has a second rectilinear planar surface, and wherein the second blade is configured to move in a reciprocating manner in opposite directions that are parallel to the longitudinal axis of the shaft body; and a handle coupled to the proximal end of the shaft; wherein the shaft, the first blade, and the second blade are sized for insertion into a patient.

Item 2: The shaft comprises a first elongated member and a second elongated member, wherein the first blade is fixedly coupled to the first elongated member, and wherein the second blade is fixedly coupled to the second elongated member, and wherein the second elongated member is moveable along the longitudinal axis relative to the first elongated member.

Item 3: The first elongated member comprises an outer tube, and the second elongated member comprises an inner elongated member disposed inside the outer tube.

Item 4: The second elongated member comprises a proximal member end, and a spherical connector at, or coupled to, the proximal member end.

Item 5: The handle comprises a user control mechanically coupled to the spherical connector.

Item 6: The spherical connector is configured to allow the user control to actuate the second blade while also allowing the second elongated member to rotate about the longitudinal axis relative to the user control.

Item 7: The medical device further includes a spring coupled to the second elongated member, wherein the spring is configured to apply a spring force in a direction that is opposite to a movement direction of the second elongated member.

Item 8: One of the first blade and the second blade comprises a protrusion, and another one of the first blade and the second blade comprises a slot for moveably accommodating the protrusion.

Item 9: The first blade comprises a serrated cutting edge.

Item 10: The second blade comprises a serrated cutting edge.

Item 11: The first blade comprises a plurality of indicators for indicating different respective degrees of tissue-penetration.

Item 12: The handle comprises a knob configured to rotate the shaft about the longitudinal axis.

Item 13: The knob is rotatable about the longitudinal axis.

Item 14: The handle comprises a user control configured to move the second blade.

Item 15: The user control comprises a pump trigger.

Item 16: The user control is moveable in a first actuation direction in response to pressure applied at the user control by a user, and is moveable in a second direction that is opposite to the first actuation direction in response to the user releasing the pressure applied at the user control.

Item 17: The user control is configured to move the second blade back-and-forth once in response to each instance of pressure applied at the user control followed by a release of the applied pressure.

Item 18: The user control is configured to move the second blade back-and-forth multiple times in response to each instance of pressure applied at the user control followed by a release of the applied pressure.

Item 19: The handle comprises a port in fluid communication with the distal end of the shaft.

Item 20: The shaft, the first blade, and the second blade are sized for insertion into a uterus.

Item 21: The medical device further includes a camera configured to view the first blade and an environment around the first blade.

Item 22: The medical device further includes a light source configured to illuminate an area around the first blade and/or the second blade.

Item 23: The medical device further includes a motor for actuating the second blade.

Item 24: The medical device further includes a cam with an asymmetric configuration, wherein the motor is configured to rotate the cam.

Item 25: A method performed by a medical device, the medical device having a shaft, a first blade, and a second blade that is in contact with the first blade, wherein the first blade is fixedly coupled to a distal end of the shaft, wherein the shaft, the first blade, and the second blade are sized for insertion into a patient, wherein the first blade has a first rectilinear planar surface, and wherein the second blade has a second rectilinear planar surface, includes: cutting tissue at a target site inside the patient by moving the second blade relative to the first blade in a first direction that is parallel to a longitudinal axis of the shaft; and moving the second blade relative to the first blade in a second direction that is parallel to the longitudinal axis of the shaft, the second direction being opposite from the first direction.

Item 26: The first blade is fixedly coupled to a first elongated member, and the second blade is fixedly coupled to a second elongated member, and wherein the moving of the second blade in the first direction is caused by a movement of the second elongated member relative to the first elongated member.

Item 27: The first elongated member comprises an outer tube, and the second elongated member comprises an inner elongated member disposed inside the outer tube.

Item 28: The second elongated member comprises a proximal member end, and a spherical connector at, or coupled to, the proximal member end.

Item 29: The medical device also comprises a handle with a user control mechanically coupled to the spherical connector, and wherein a movement of the second blade in the first direction and/or the second direction is in response to an actuation of the user control.

Item 30: The spherical connector is configured to allow the user control to actuate the second blade while also allowing the second elongated member to rotate about the longitudinal axis relative to the user control.

Item 31: The method further includes providing a spring force by a spring in a direction that is opposite to a movement direction of the second elongated member.

Item 32: The method further includes guiding a movement of the second blade relative to the first blade, wherein the act of guiding is performed by a protrusion at one of the first blade and the second blade, the protrusion being accommodated in a slot at another one of the first blade and the second blade.

Item 33: The tissue is cut by a serrated cutting edge of the first blade.

Item 34: The tissue is cut by a serrated cutting edge of the second blade.

Item 35: The method further includes providing, by the first blade, a plurality of indicators for indicating different respective degrees of tissue-penetration.

Item 36: The method further includes changing an orientation of the first blade and the second blade, by a rotation of the shaft about the longitudinal axis.

Item 37: The medical device comprises a knob that is rotatable about the longitudinal axis, the knob configured to rotate the shaft about the longitudinal axis.

Item 38: A movement of the second blade in the first direction and/or the second direction is provisioned by a user control at a handle of the medical device.

Item 39: The user control comprises a pump trigger.

Item 40: The user control is moveable in a first actuation direction in response to pressure applied at the user control by a user, and is moveable in a second direction that is opposite to the first actuation direction in response to the user releasing the pressure applied at the user control.

Item 41: The second blade is moved back-and-forth once in response to each instance of pressure applied at the user control followed by a release of the applied pressure.

Item 42: The second blade is moved back-and-forth multiple times in response to each instance of pressure applied at the user control followed by a release of the applied pressure.

Item 43: The method further includes delivering fluid from the distal end of the shaft to a proximal end of the shaft.

Item 44: The act of cutting the tissue is performed inside a uterus.

Item 45: The method further includes: illuminating the target site inside the patient; and imaging, by a camera, the first blade and an environment around the first blade.

Item 46: The act of illuminating is performed by a light source.

Item 47: A movement of the second blade in the first direction and/or the second direction is caused by a motor.

Item 48: The method further includes rotating a cam, by the motor, wherein the cam has an asymmetric configuration.

Item 49: A surgical device for cutting tissue, includes: a handle; a shaft coupled to a distal portion of the handle; a planar stationary cutting instrument fixedly coupled to a distal portion of the shaft, wherein the stationary cutting instrument has a first cutting edge on one side thereof; a planar moveable cutting instrument slideably coupled to the distal portion of the shaft, wherein the moveable cutting instrument has a second cutting edge on one side thereof, and wherein the first cutting edge and second cutting edge face the same direction; and a drive coupled to the moveable cutting instrument to translate and reciprocate the moveable cutting instrument relative to the stationary cutting instrument in response to a force applied to the drive and to cut tissue during translation and reciprocation of the moveable cutting instrument.

Item 50: The shaft comprises a first elongated member and a second elongated member, wherein the stationary cutting instrument is fixedly coupled to the first elongated member, and wherein the moveable cutting instrument is fixedly coupled to the second elongated member, and wherein the second elongated member is moveable along a longitudinal axis of the shaft relative to the first elongated member.

Item 51: The first elongated member comprises an outer tube, and the second elongated member comprises an inner elongated member disposed inside the outer tube.

Item 52: The second elongated member comprises a proximal member end, and a spherical connector at, or coupled to, the proximal member end.

Item 53: The handle comprises a user control mechanically coupled to the spherical connector.

Item 54: The spherical connector is configured to allow the user control to actuate the moveable cutting instrument while also allowing the second elongated member to rotate about the longitudinal axis relative to the user control.

Item 55: The surgical device further includes a spring coupled to the second elongated member, wherein the spring is configured to apply a spring force in a direction that is opposite to a movement direction of the second elongated member.

Item 56: One of the stationary cutting instrument and the moveable cutting instrument comprises a protrusion, and another one of the stationary cutting instrument and the moveable cutting instrument comprises a slot for moveably accommodating the protrusion.

Item 57: The first cutting edge comprises a serrated cutting edge.

Item 58: The second cutting edge comprises a serrated cutting edge.

Item 59: The stationary cutting instrument comprises a plurality of indicators for indicating different respective degrees of tissue-penetration.

Item 60: The handle comprises a knob configured to rotate the shaft about a longitudinal axis of the shaft.

Item 61: The knob is rotatable about the longitudinal axis of the shaft.

Item 62: The handle comprises a user control configured to move the moveable cutting instrument.

Item 63: The user control comprises a pump trigger.

Item 64: The user control is moveable in a first actuation direction in response to pressure applied at the user control by a user, and is moveable in a second direction that is opposite to the first actuation direction in response to the user releasing the pressure applied at the user control.

Item 65: The user control is configured to move the moveable cutting instrument back-and-forth once in response to each instance of pressure applied at the user control followed by a release of the applied pressure.

Item 66: The user control is configured to move the moveable cutting instrument back-and-forth multiple times in response to each instance of pressure applied at the user control followed by a release of the applied pressure.

Item 67: The handle comprises a port in fluid communication with a distal end of the shaft.

Item 68: The shaft, the stationary cutting instrument, and the moveable cutting instrument are sized for insertion into a uterus.

Item 69: The surgical device further includes a camera configured to view the stationary cutting instrument and an environment around the stationary cutting instrument.

Item 70: The surgical device further includes a light source configured to illuminate an area around the stationary cutting instrument and/or the moveable cutting instrument.

Item 71: The surgical device further includes a motor for actuating the moveable cutting instrument.

Item 72: The surgical device further includes a cam with an asymmetric configuration, wherein the motor is configured to rotate the cam.

Item 73: A method for cutting tissue, includes: inserting a distal portion of a surgical device tangentially against targeted tissue, the surgical instrument having a first planar cutting member and a second planar cutting member, the first planar cutting member having a first cutting edge, the second planar cutting member having a second cutting edge; translating the second planar cutting member relative to the first planar cutting member, wherein during the act of translating, the first cutting edge and the second cutting edge shear the targeted tissue; and reciprocating the second planar cutting member relative to the first planar cutting member.

Item 74: The first planar cutting member is fixedly coupled to a first elongated member, and the second planar cutting member is fixedly coupled to a second elongated member, and wherein the translating of the second planar cutting member is caused by a movement of the second elongated member relative to the first elongated member.

Item 75: The first elongated member comprises an outer tube, and the second elongated member comprises an inner elongated member disposed inside the outer tube.

Item 76: The second elongated member comprises a proximal member end, and a spherical connector at, or coupled to, the proximal member end.

Item 77: The surgical device also comprises a handle with a user control mechanically coupled to the spherical connector, and wherein a translational movement of the second planar cutting member is in response to an actuation of the user control.

Item 78: The spherical connector is configured to allow the user control to actuate the second planar cutting member while also allowing the second elongated member to rotate about a longitudinal axis of the first elongated member relative to the user control.

Item 79: The method further includes providing a spring force by a spring in a direction that is opposite to a movement direction of the second planar cutting member.

Item 80: The method further includes guiding a movement of the second planar cutting member relative to the first planar cutting member, wherein the act of guiding is performed by a protrusion at one of the first planar cutting member and the second planar cutting member, the protru-sion being accommodated in a slot at another one of the first planar cutting member and the second planar cutting member.

Item 81: The first cutting edge comprises a serrated cutting edge.

Item 82: The second cutting edge comprises a serrated cutting edge.

Item 83: The method further includes providing, by the first planar cutting member, a plurality of indicators for indicating different respective degrees of tissue-penetration.

Item 84: The method further includes changing an orientation of the first planar cutting member and the second planar cutting member, by a rotation of a shaft about a longitudinal axis of the shaft.

Item 85: The surgical device comprises a knob that is rotatable about the longitudinal axis of the shaft, the knob configured to rotate the shaft about the longitudinal axis.

Item 86: A movement of the second planar cutting member is provisioned by a user control at a handle of the surgical device.

Item 87: The user control comprises a pump trigger.

Item 88: The user control is moveable in a first actuation direction in response to pressure applied at the user control by a user, and is moveable in a second direction that is opposite to the first actuation direction in response to the user releasing the pressure applied at the user control.

Item 89: The second planar cutting member is moved back-and-forth once in response to each instance of pressure applied at the user control followed by a release of the applied pressure.

Item 90: The second planar cutting member is moved back-and-forth multiple times in response to each instance of pressure applied at the user control followed by a release of the applied pressure.

Item 91: The method further includes delivering fluid from a distal end of the surgical device to a proximal end of the surgical device.

Item 92: The targeted tissue is inside a uterus.

Item 93: The method further includes: illuminating targeted tissue; and imaging, by a camera, the first planar cutting member and an environment around the first planar cutting member.

Item 94: The act of illuminating is performed by a light source.

Item 95: A movement of the second planar cutting member is caused by a motor.

Item 96: The method further includes rotating a cam, by the motor, wherein the cam has an asymmetric configuration.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents thereof.

The invention claimed is:

1. A medical device, comprising:
a shaft having a distal end, a proximal end, and a shaft body extending between the distal end and the proximal end, the shaft body having a longitudinal axis;
a first blade fixedly coupled to the shaft, wherein the first blade has a first rectilinear planar surface;

a second blade in contact with the first blade, wherein the second blade has a second rectilinear planar surface, and wherein the second blade is configured to move in a reciprocating manner in opposite directions that are parallel to the longitudinal axis of the shaft body; and a handle coupled to the proximal end of the shaft;

wherein the first blade and the second blade are sized for insertion into a patient;

wherein the medical device further comprises a mechanical coupler configured to maintain contact between the first blade and the second blade while allowing the second blade to translate relative to the first blade;

wherein the handle comprises a user control configured to move the second blade; and wherein the handle comprises a hand-held portion and a knob rotatable relative to the hand-held portion, the knob configured to rotate the shaft about the longitudinal axis.

2. The medical device of claim 1, wherein the shaft comprises a first elongated member and a second elongated member, wherein the first blade is coupled to the first elongated member, and wherein the second blade is coupled to the second elongated member.

3. The medical device of claim 2, wherein the first elongated member comprises an outer tube, and the second elongated member comprises an inner elongated member disposed inside the outer tube.

4. The medical device of claim 2, wherein the second elongated member comprises a spherical connector.

5. The medical device of claim 4, wherein the user control is mechanically coupled to the spherical connector.

6. The medical device of claim 5, wherein the spherical connector is configured to allow the user control to actuate the second blade, while also allowing the second elongated member to rotate about the longitudinal axis relative to the user control.

7. The medical device of claim 2, further comprising a spring coupled to the second elongated member, wherein the spring is configured to apply a spring force in a direction that is opposite to a movement direction of the second elongated member.

8. The medical device of claim 1, wherein the mechanical coupler comprises a protrusion integrally extending from one of the first blade and the second blade, and wherein another one of the first blade and the second blade comprises a slot for moveably accommodating the protrusion.

9. The medical device of claim 1, wherein the first blade comprises a first serrated cutting edge, and wherein the second blade comprises a second serrated cutting edge.

10. The medical device of claim 1, wherein the first blade comprises a plurality of indicators for indicating different respective degrees of tissue-penetration.

11. The medical device of claim 1, wherein the user control comprises a trigger.

12. The medical device of claim 1, wherein the user control is moveable in a first actuation direction in response to pressure applied at the user control by a user, and is moveable in a second direction that is opposite to the first actuation direction in response to the user releasing the pressure applied at the user control.

13. The medical device of claim 1, wherein the user control is configured to move the second blade back-and-forth only once in response to each instance of pressure applied at the user control followed by a release of the applied pressure.

14. The medical device of claim 1, wherein the user control is configured to move the second blade back-and-forth multiple times in response to each instance of pressure applied at the user control followed by a release of the applied pressure.

15. The medical device of claim 1, wherein the handle comprises a port in fluid communication with the distal end of the shaft.

16. The medical device of claim 1, wherein the shaft, the first blade, and the second blade are sized for insertion into a uterus.

17. The medical device of claim 1, further comprising a motor for actuating the second blade.

18. The medical device of claim 17, further comprising a cam with an asymmetric configuration, wherein the motor is configured to rotate the cam.

19. The medical device of claim 1, wherein the first blade has a first cutting edge on one side thereof, wherein the second blade has a second cutting edge on one side thereof, and wherein the first cutting edge and second cutting edge face a same direction.

20. A medical device, comprising:

a shaft having a distal end, a proximal end, and a shaft body extending between the distal end and the proximal end, the shaft body having a longitudinal axis;

a first blade fixedly coupled to the shaft, wherein the first blade has a first rectilinear planar surface;

a second blade in contact with the first blade, wherein the second blade has a second rectilinear planar surface, and wherein the second blade is configured to move in a reciprocating manner in opposite directions that are parallel to the longitudinal axis of the shaft body; and a handle coupled to the proximal end of the shaft;

wherein the shaft comprises a first elongated member and a second elongated member, wherein the first blade is coupled to the first elongated member, and wherein the second blade is coupled to the second elongated member, and wherein the second elongated member is moveable along the longitudinal axis relative to the first elongated member;

wherein the second elongated member comprises a proximal member end, and a spherical connector at, or coupled to, the proximal member end;

wherein the handle comprises a user control mechanically coupled to the spherical connector; and wherein the spherical connector is configured to allow the user control to actuate the second blade, while also allowing the second elongated member to rotate about the longitudinal axis relative to the user control.

* * * * *